US012685590B2

(12) United States Patent
Block

(10) Patent No.: US 12,685,590 B2
(45) Date of Patent: Jul. 21, 2026

(54) LASER FIBER DISPLACEMENT SYSTEM AND METHODS

(71) Applicant: Medtronic Navigation, Inc., Louisville, CO (US)

(72) Inventor: Orey Block, Louisville, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 808 days.

(21) Appl. No.: 17/996,607

(22) PCT Filed: Apr. 30, 2021

(86) PCT No.: PCT/US2021/030279
§ 371 (c)(1),
(2) Date: Oct. 19, 2022

(87) PCT Pub. No.: WO2021/225903
PCT Pub. Date: Nov. 11, 2021

(65) Prior Publication Data
US 2023/0248433 A1 Aug. 10, 2023

Related U.S. Application Data

(60) Provisional application No. 63/019,815, filed on May 4, 2020.

(51) Int. Cl.
*A61B 18/24* (2006.01)
*A61B 17/00* (2006.01)
(Continued)

(52) U.S. Cl.
CPC ..... *A61B 18/24* (2013.01); *A61B 2017/00911* (2013.01); *A61B 2018/00023* (2013.01);
(Continued)

(58) Field of Classification Search
CPC .......... A61B 18/24; A61B 2017/00911; A61B 2018/00023; A61B 2018/00577; A61B 2018/206
(Continued)

(56) References Cited

U.S. PATENT DOCUMENTS 5,409,483 A * 4/1995 Campbell ............ A61N 5/0601
606/15
6,418,337 B1 * 7/2002 Torchia .................. A61B 18/24
606/17
(Continued)

FOREIGN PATENT DOCUMENTS

CN 110290757 9/2019
WO 2018156522 A1 8/2018
WO 2019171336 A1 9/2019

OTHER PUBLICATIONS

Official Action with English Translation for China Patent Application No. 202180027794.9, dated Jun. 4, 2025, 19 pages.
(Continued)

*Primary Examiner* — Aaron F Roane
(74) *Attorney, Agent, or Firm* — Sheridan Ross PC

(57) ABSTRACT

Systems and methods used to ablate tissues using laser energy are disclosed. The systems and methods may be configured to remotely displace a laser fiber to ablate more than one zone of tissue. The systems can include a displacement device comprising a linear displacement member configured to longitudinally displace the laser fiber. The systems can also include a sleeve configured to maintain a cooling catheter in a longitudinal stationary position when the laser fiber is displaced.

20 Claims, 5 Drawing Sheets

(51) Int. Cl.
   *A61B 18/00* (2006.01)
   *A61B 18/20* (2006.01)
(52) U.S. Cl.
   CPC ............... *A61B 2018/00577* (2013.01); *A61B 2018/206* (2013.01)
(58) Field of Classification Search
   USPC ......................................................... 606/15
   See application file for complete search history.

(56) References Cited

U.S. PATENT DOCUMENTS

| | | | |
|---|---|---|---|
| 7,167,741 | B2 | 1/2007 | Torchia et al. |
| 7,778,682 | B2 | 8/2010 | Kumar et al. |
| 8,275,443 | B2 | 9/2012 | Goldenberg et al. |
| 8,728,092 | B2 | 5/2014 | Qureshi et al. |
| 9,539,058 | B2 | 1/2017 | Tsekos et al. |
| 9,700,342 | B2 | 7/2017 | Andrews et al. |
| 10,092,367 | B2 | 10/2018 | Andrews et al. |
| 10,130,427 | B2 | 11/2018 | Tanner et al. |
| 10,188,462 | B2 | 1/2019 | Tyc et al. |
| 10,869,721 | B2 | 12/2020 | Gowda et al. |
| 2003/0023236 | A1* | 1/2003 | Gowda .................. A61B 18/24 606/15 |
| 2005/0209589 | A1 | 9/2005 | Berman et al. |
| 2006/0287647 | A1 | 12/2006 | Tochia et al. |
| 2012/0259201 | A1* | 10/2012 | Chen ................ G01R 33/56358 600/411 |
| 2014/0163664 | A1* | 6/2014 | Goldsmith ......... A61B 17/0057 604/93.01 |
| 2016/0302868 | A1 | 10/2016 | Nagale et al. |
| 2017/0367776 | A1 | 12/2017 | Kwok et al. |
| 2018/0132954 | A1 | 5/2018 | Nazim et al. |
| 2020/0147299 | A1 | 5/2020 | Piferi |

OTHER PUBLICATIONS

Official Action for European Patent Application No. 21727673.2, dated Dec. 12, 2025, 5 pages.

* cited by examiner

LASER FIBER DISPLACEMENT SYSTEM AND METHODS

RELATED APPLICATIONS

The present application is a National Stage of International Application No. PCT/US2021/030279, filed Apr. 30, 2021, which claims priority to U.S. Provisional Application No. 63/019,815, filed on May 4, 2020, which are hereby incorporated by reference in their entireties.

TECHNICAL FIELD

The present disclosure relates generally to devices, systems, and methods used to treat a patient's tissue. More specifically, in some embodiments, the present disclosure relates to devices, systems, and methods used to manipulate or displace a laser fiber to ablate the patient's tissue at different locations while the patient is in a magnetic resonance imaging environment.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
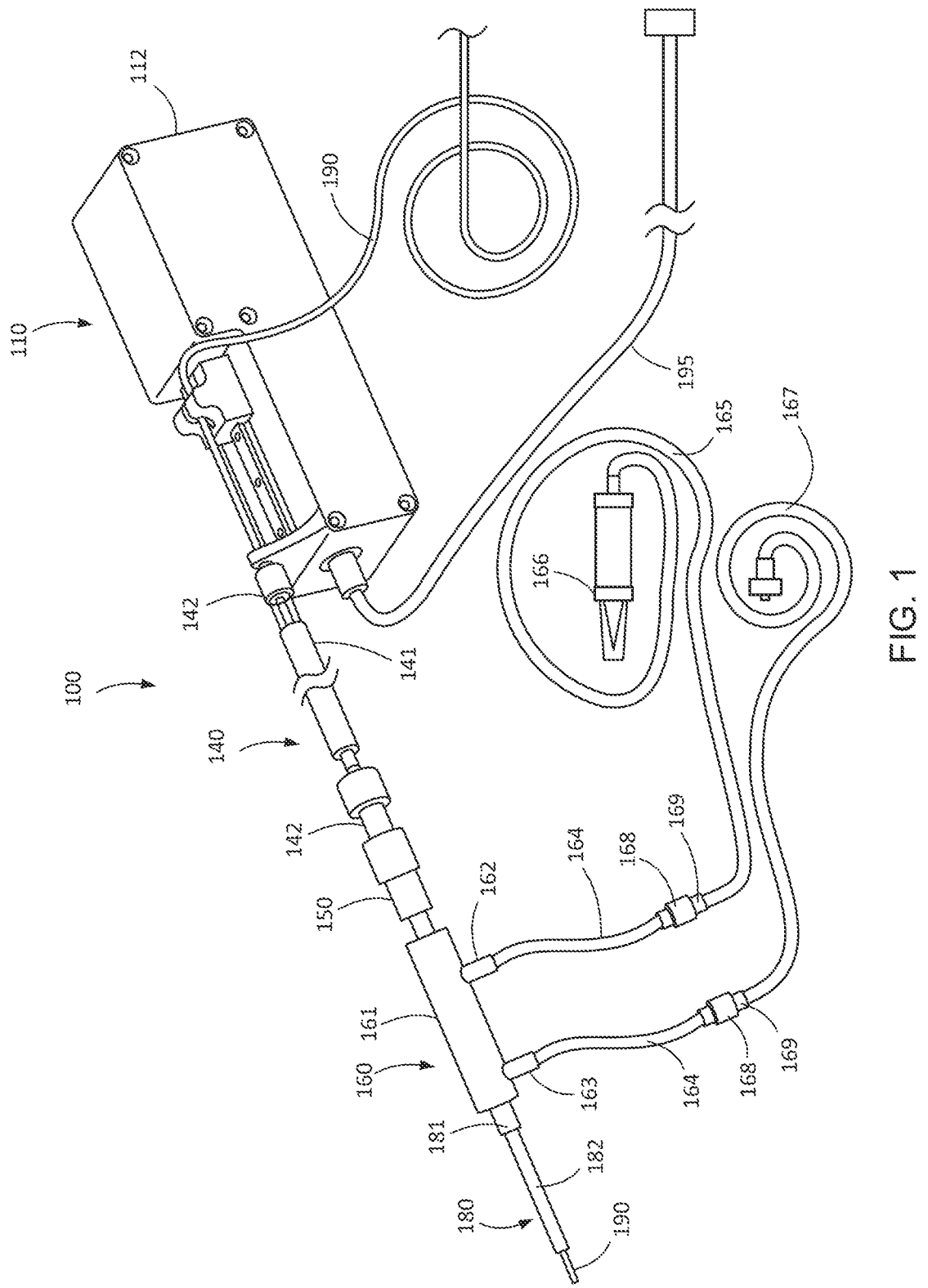
FIG. 1 is a perspective view of an embodiment of a laser fiber displacement system.

During some therapies, lesion or tumor tissue may be treated by catheter-based laser ablation, including treatments where a laser fiber disposed within in a catheter is used to deliver ablation energy to the tissue. In some instances, laser energy is transmitted through the laser fiber and transfused into the tissue of the lesion. The diffused laser energy may then heat and destroy the tissue of the lesion.

Laser ablation may be performed with the assistance of magnetic resonance imaging (MRI). For instance, initial positioning and repositioning of the laser fiber within the lesion may be facilitated by use of MRI. Additionally, the MRI may be used to track temperature of the tissue using MRI thermometry. In certain instances, a treatment may include multiple applications of the laser energy due, for example, to the size of the lesion. Typically to reposition the laser fiber for additional applications of the laser energy, a practitioner manually slides the laser fiber back along the catheter. However, manual manipulation requires the practitioner to climb into the bore of the MRI magnet which is small and difficult to access. The accuracy of manual repositioning is reduced by limited visibility and difficult accessibility. Additionally, the practitioner may unintentionally alter the position of the catheter.

A laser fiber displacement system may pull back, withdraw, or otherwise displace the laser fiber with respect to the catheter without a practitioner entering the MRI room to manually adjust the laser fiber. In some embodiments, a laser fiber displacement system includes a displacement device and a sleeve. The sleeve may be selectively coupled to a cooling catheter. A laser fiber is received through a lumen in the sleeve and selectively coupled to the displacement device. In some instances, the displacement device is configured to longitudinally displace the laser fiber while the cooling catheter remains in a stationary state. The sleeve may provide a buffer to limit the transfer of movement from the displacement device and laser fiber to the cooling catheter. Notwithstanding the use of the terms "pull back" and "withdraw," devices and systems within the scope of this disclosure may be configured to displace a laser fiber in any direction with respect to a catheter. Thus, disclosure herein referring to pulling or retracting a fiber may be analogously applied to advancing or otherwise displacing the fiber with respect to a catheter.

The sleeve may be longitudinally non-compressible. Additionally, the displacement system may comprise magnetic resonance (MR) safe or conditional components such that the displacement system can be used in a magnetic resonance imaging (MRI) environment. The displacement system may additionally include a sealing member configured to form a seal around the laser fiber and a tubing set configured to deliver fluid to and receive fluid from the cooling catheter.

The displacement device may include a housing, a linear displacement member, a controller, a communication member, and a power source. The linear displacement member may include a slide, a carriage, a clamp, and a motor. A communication cable can be coupled to the displacement device to facilitate activation of the motor from a remote location outside of the MRI environment. The displacement device can include MR safe or conditional components.

In some embodiments, a method of ablating a patient's tissue at multiple locations may include various steps. For example, a procedure may include inserting a laser fiber and a cooling catheter into a target ablation region. In some instances, a sleeve may couple the laser fiber displacement system to the cooling catheter. The cooling catheter may be inserted into the patient such that a distal portion of the cooling catheter is adjacent to and/or directed towards tissue targeted for ablation (e.g., lesion or tumor). The laser fiber may be disposed through the cooling catheter such that a distal portion is positioned adjacent a first zone of tissue to be ablated. The laser fiber may be coupled to a linear displacement member, such as a linear actuator, of the laser fiber displacement system. For example, the laser fiber may be coupled to a clamp of a displacement device. Laser energy may be transmitted through the laser fiber to ablate a first zone of tissue. The linear actuator may then be remotely activated via a communication cable to displace (such as to proximally pull back) the laser fiber relative to the first ablation tissue zone. The laser fiber may thus be positioned adjacent a second zone of tissue to be ablated. While the laser fiber being repositioned, the cooling catheter may remain stationary with respect to the patient's body. Laser energy may then be transmitted through the laser fiber to ablate the second zone of tissue. One or more of these steps may be repeated to ablate a plurality of target zones during a single therapy. Methods including any subset of these steps are likewise within the scope of this disclosure.

Embodiments described herein may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device closest to or within the patient during use. The proximal end refers to the opposite end, or the end farthest from the patient. For example, as specifically applied to the sleeve portion of a laser fiber displacement system, the distal end of the sleeve refers to the end nearest the patient and the proximal end refers to the opposite end, the end farthest from the patient.

"Fluid" is used in its broadest sense, to refer to any fluid, including both liquids and gases as well as solutions, compounds, suspensions, etc., which generally behave as fluids.

FIGS. 1-5 illustrate different views of a laser fiber displacement system and related components. In certain views each component may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
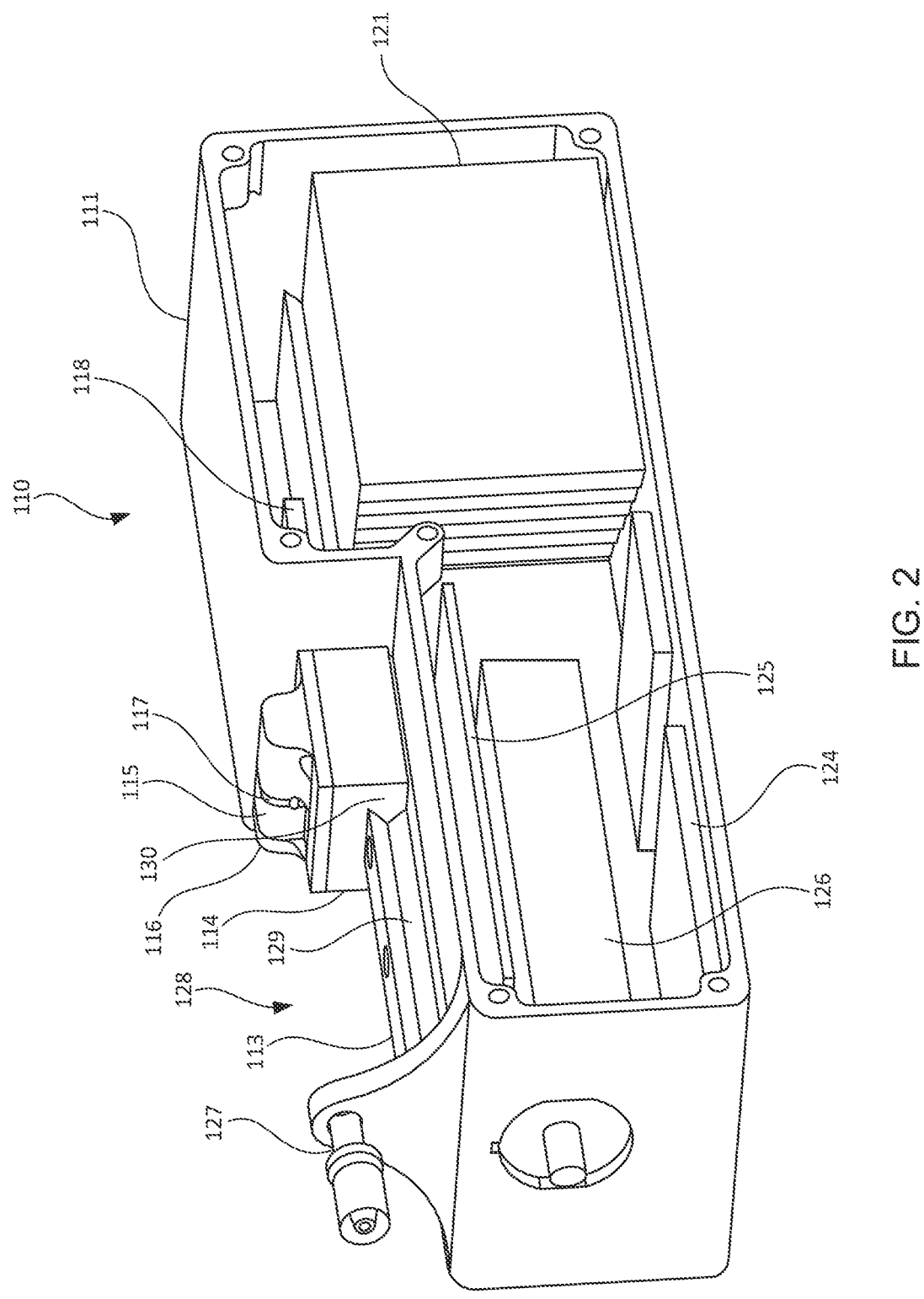
FIG. 2 is a perspective front view of a displacement device of the laser fiber displacement system of FIG. 1 with the housing cover removed.
Figure 3:
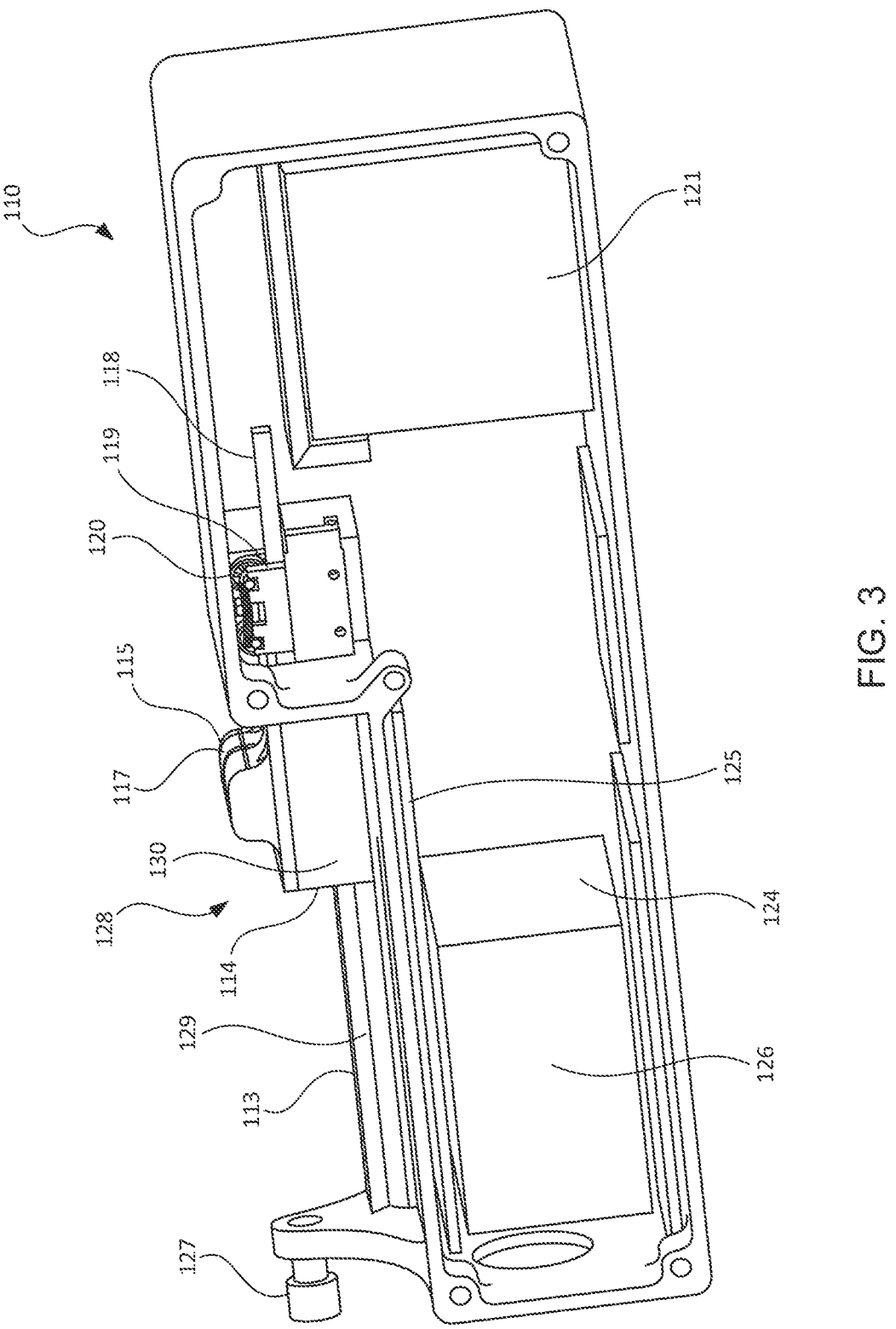
FIG. 3 is a perspective rear view of the displacement device of the laser fiber displacement system of FIG. 1 with the housing cover removed.

FIGS. 1-3 depict an embodiment of laser fiber displacement system 100. In the illustrated embodiment, the laser fiber displacement system 100 comprises a displacement device 110, a sleeve 140, a sealing member 150, a tubing set 160, and a communication cable 195.

The displacement device 110 may comprise a housing 111, a linear displacement member 128, a power source 121, a power source management member 123, a motor controller 124, a voltage regulator 125, and a communication member 126. As illustrated, the housing 111 comprises walls and a removeable cover 112. The walls and cover 112 define a cavity configured to receive certain components of the displacement device 110 while other components are coupled to an exterior surface of the housing 111. For example, the power source 121, motor controller 124, communication member 126, and a portion of the linear displacement member 128 may be disposed within the cavity while another portion of the linear displacement member 128 may be disposed on the exterior surface, as shown in FIGS. 2 and 3. The housing 111 can be formed of any suitable, non-magnetic material. Exemplary materials may include polymers such as polyethylene, polypropylene, polycarbonate, etc. and metals, such as aluminum, copper, etc. The housing 111 may be configured to be disposed on a flat surface, such as a tabletop, that is positioned adjacent a patient.

In some embodiments, the linear displacement member 128 comprises a linear actuator. In some embodiments, the linear displacement member 128 may comprise a slide 113, a carriage 114, a clamp 115, an actuator member 118, and a motor 119. The linear displacement member 128 may be configured to longitudinally displace or reposition a laser fiber 190 during a tissue treatment procedure, such as tissue ablation. As depicted in FIGS. 2 and 3, in the illustrated embodiment, the slide 113 is disposed on the exterior surface of the housing 111 and oriented with a longitudinal axis of the housing 111. The slide 113 includes elongate channels 129 disposed on opposing sides of the slide 113 and extending substantially along a length of the slide 112. The channels 129 are configured to slidingly engage with the carriage 114 and to retain the carriage 114 in engagement with the slide 113. The channels 129 may be of any suitable shape, such as square, rectangular, V-shape, circular, etc. The slide 113 may be formed from any suitable material, including lubricious or self-lubricating materials. For example, the slide 113 may be formed from high density polyethylene, polyoxymethylene, etc. Additionally or alternatively, in some embodiments, a lubricious coating may be applied to an upper surface of the slide 113.

In the illustrated embodiment, the carriage 114 is slidingly disposed on an upper surface of the slide 113. The carriage 114 includes retaining arms 130 that extend from a bottom surface and engage with the channels 129 of the slide 113. Ends of the arms 130 can be shaped to mate with the channels 129. The carriage 114 may be formed from the same material as the slide 113 or may be formed of different materials. In some embodiments, a lubricious coating may be applied to the bottom surface of the carriage 114.

As depicted in the illustrated embodiment, the clamp 115 may be disposed on a top surface of the carriage 114. In other embodiments, the clamp 115 may be disposed on another suitable surface of the carriage 114, such as a side surface. The clamp 115 is configured to selectively secure the laser fiber 190 to the carriage 114 such that the laser fiber 190 can be selectively longitudinally displaced. The clamp 115 includes a clamp actuator 116 and a slot 117. In the illustrated embodiment, the slot 117 is configured to receive the laser fiber 190 and the clamp actuator 116 is configured to actuate the clamp 115 to apply a clamping force to the laser fiber 190. The clamping force may be configured to secure the laser fiber 190 for longitudinal displacement while preventing damage to the laser fiber 190 that could disrupt the transmission of laser energy through the laser fiber 190. In other words, the magnitude of the force applied by the clamp 115 may be tuned to secure the laser fiber 190 without damaging or interfering with the function of the laser fiber 190. The clamp actuator 116 may be rotated by the user to provide the clamping force. In some embodiments, the clamp actuator 116 may utilize electromagnets, static magnets, a resilient member, etc. to provide the clamping force. Other configurations of the clamp 115 are within the scope of this disclosure.

The motor 119 may be any suitable type of non-magnetic, servomotor coupled to an encoder and configured to utilize position feedback to control its motion and position. For example, the motor 119 may be a piezo linear motor, piezo rotation motor, a Piezo LEGS® motor, a stepper motor, etc. The motor 119 may be configured to longitudinally displace the carriage 114 and the laser fiber 190 to along a continuous range and may be configured to position the laser fiber with an accuracy of plus or minus 5 mm. The motor 119 may be coupled to the carriage 114 via the actuator member 118. As depicted in the illustrated embodiment, the actuator member 118 may be in the form of an elongate rod. In the illustrated embodiment, the actuator member 118 is fixedly coupled to the carriage and moveably coupled to the motor 119. When the motor 119 is activated, the motor 119 linearly displaces the actuator member 118 via the drive mechanism 120 which longitudinally displaces the carriage 114.

In other embodiments, the actuator member 118 may be in the form of a lead screw. In such embodiments, the actuator member 118 may be fixedly coupled to the motor 119 and rotationally coupled to the carriage 114. When the motor 119 is activated, the motor rotates the actuator member 119 which longitudinally displaces the carriage 114. In other embodiments, the linear displacement member 128 may be configured in any suitable way that facilitates linear displacement of the carriage 114. For example, the linear actuator member may include a gear rack and a gear pinion, a timing belt, etc.

Activation and control of the motor 119 may be accomplished via a motor controller 124, including a motor controller 124 comprising a printed circuit board. Electrical power for the motor 119 may be provided by a power source 121. In some embodiments, the power source 121 can be a plurality of battery cells connected in series to provide an output of about 40 volts to about 55 volts. For example, the power source 121 may include thirteen 1200 mAH litho/polymer cells. Other types of battery cells or sources of electrical power are contemplated within the scope of this disclosure. The power source 121 may be either rechargeable by an external recharging member or non-rechargeable and replaceable. A voltage regulator 125 can regulate the voltage output of the power source to about 48 volts. In certain embodiments, the pull device 110 may include an integrated battery charged disposed within the housing 111.

An electronic communication member 126 may be coupled to the motor controller 124. The communication member 126 can be of any suitable type, such as an optical to serial converter, a USB to serial converter, etc. The communication member 126 can receive communications from a remote computer to activate and control the motor 119 through the motor controller 124. A communication cable 195 can be coupled to the communication member 126. The communication cable 195 can be of any suitable type. For example, the communication cable can be a fiber optic cable or a copper wire cable.

As illustrated in FIG. 1, the sleeve 140 may be coupled to the displacement device 110 via a connector 142. In some embodiments, the connector 127 may include a male luer lock fitting. The sleeve 140 may comprise a tubular elongate body 141 with connectors 142 disposed at opposing ends of the elongate body 141. In some instances, the elongate body 141 is configured to resist longitudinal compression when the laser fiber 190 is pulled back during use. In other words, a length of the elongate body 141 may be configured to be substantially maintained when the laser fiber is pulled back by the displacement device 110. The elongate body 141 may be formed from any suitable material, such as nylon, polyethylene, polypropylene, etc. The connectors 142 can include female luer lock fittings configured to selectively couple with the connector 127.

A sealing member 150 is coupled to the connector 142 disposed at a distal end of the sleeve 140. Alternatively, the sealing member 150 may be coupled directly to the elongate body 141. In the illustrated embodiment, the sealing member 150 is in fluid communication with the sleeve 140. The sealing member 150 is configured to selectively form a fluid tight seal around the laser fiber 190 to prevent leakage of fluid from the tubing set 160. The sealing member 150 may also be configured to permit slippage of the laser fiber 190 through the sealing member 150 when the sealing member 150 is sealed around the laser fiber 190. An exemplary embodiment of the sealing member 150 may be a Toughy-Borst adapter. In some embodiments, the sealing member 150 may include, for example, an O-ring sized to allow passage of and to seal around the laser fiber 190. Other embodiments of the sealing member 150 are contemplated within the scope of this disclosure.

The tubing set 160 may be coupled to a distal end of the sealing member 150. The tubing set 160 may be fluidly coupled to the cooling catheter 180 and provide fluid to the cooling catheter 180 to control a temperature of the cooling catheter 180. The tubing set 160 can cycle a fluid (e.g., saline) through the cooling catheter 180 that is coupled to the tubing set 160. The fluid can cool the patient's tissue during the tissue ablation procedure. As depicted in FIG. 1, the fluid set 160 may comprise a manifold 161, inflow tubing 165, and outflow tubing 166

In the illustrated embodiments, the manifold 161 includes an inflow port 162 and an outflow port 163. An extension tube 164 is coupled to each of the inflow port 162 and outflow port 163. A connector 168 comprising a female luer fitting can be coupled to a free end of each of the extension tubes 164. The inflow tubing 165 includes a connector 169 configured to selectively couple with the connector 168 of the inflow extension tube 164. The inflow tubing 165 can include a drip chamber 166 configured to couple with a fluid source. The outflow tubing 165 includes a connector 169 configured to selectively couple with the connector 168 of the outflow extension tube 164.

The laser fiber displacement system 100, may be utilized for any suitable tissue treatment. For example, the laser fiber displacement system 100 may be used to ablate a lesion (e.g., tumor) in conjunction with an MRI. The MRI can be used to confirm positioning and repositioning of the laser fiber 190.

As noted above, the laser displacement system 100 may be configured for use within a magnetic resonance (MR) environment while minimizing interference to the MR imagining. In various embodiments, the laser displacement system 100 may conform to standards for being MR Safe or MR Conditional. MR Safe, as defined by the American Society for Testing and Materials (ASTM), is defined as an item that poses no known hazards in all MR environments. MR Safe items include nonconducting, nonmagnetic items. MR Safe may thus indication that an item is 100% safe, without exception, regardless of MR system field strength or any environmental or extenuating circumstances. MR Conditional is defined by the ASTM as an item that has been demonstrated to pose no known hazards in a specified MR environment with specified conditions of use. Conditions that may be used to define the specified MR environment include field strength, spatial gradient, RF fields, specific absorption rate (SAR) as well as the potential for additional conditions such as operational conditions for a device. As an example, an item may have been tested for a 1.5-Tesla system, but not a 3-Tesla. Again, laser displacement devices 100 within the scope of this disclosure may be configured as MR Safe, MR Conditional, or may be configured to minimize interference or hazard as demonstrated by other testing or certification procedures.

The various components of the laser fiber displacement system 100, as described above, may be configured to be MR Safe or MR Conditional. This may be accomplished by utilizing components composed of non-ferromagnetic materials. For example, the components may comprise plastics and non-magnetic metals, such as non-magnetic stainless steel, copper, titanium, cobalt-chromium alloy etc.

Figure 4:
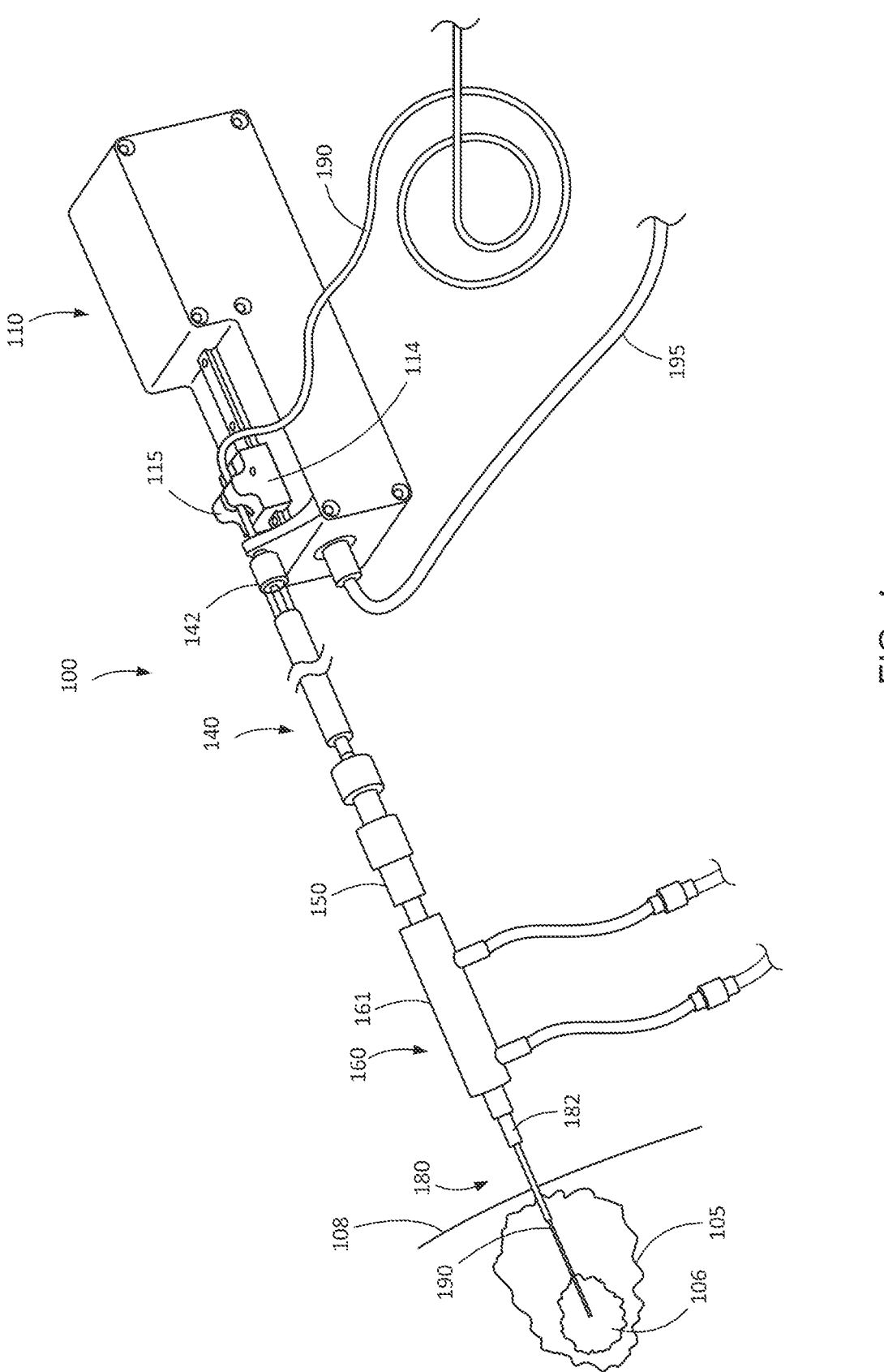
FIG. 4 is a perspective view of the laser fiber displacement system of FIG. 1 in a first ablation zone state.
Figure 5:
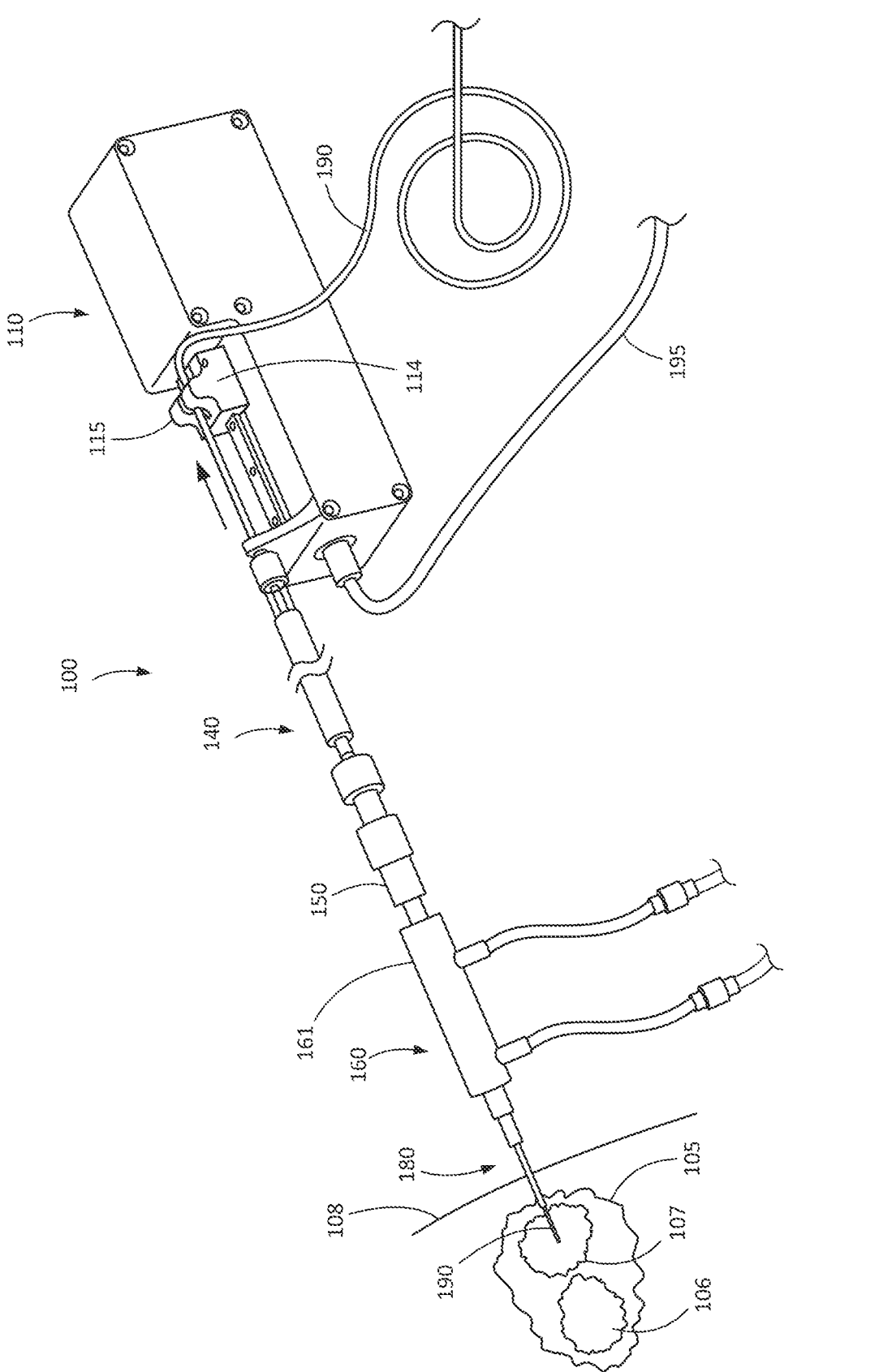
FIG. 5 is a perspective view of the laser fiber displacement system of FIG. 1 in a second ablation zone state.

FIGS. 4 and 5 illustrate one exemplary method of use of the laser fiber displacement system 100. As illustrated in FIG. 4, the laser fiber displacement system 100 is shown in a first ablation zone state. In the first ablation zone state the laser fiber displacement system 100 is coupled to the cooling catheter 180. The cooling catheter 180 is inserted through the patient's skin with a distal end disposed adjacent a lesion 105 targeted for ablation. The laser fiber 190 is shown coupled to the displacement device 110 at the clamp 115. The laser fiber 190 extends distally from the displacement device 110 and is disposed through the sleeve 140, the sealing member 150, the manifold 161 of the tubing set 160, and the cooling catheter 180. A distal portion of the laser fiber 190 is shown to be disposed within the lesion 105 and adjacent a targeted first ablation zone 106. The carriage 114 is disposed in a distal position. MRI may be used to position the cooling catheter 180 and the laser fiber 190 relative to the lesion 105 and track the temperature of the tissue during an ablation procedure.

While the laser fiber displacement system 100 is in the first ablation state, laser energy may be transmitted through the laser fiber 190. The laser energy may be diffused through the tissue of the first ablation zone 106 such that the tissue absorbs the energy and is heated, resulting in ablation or destruction of the tissue. Fluid may be delivered to and withdrawn from the cooling catheter 180 through the tubing set 160 to facilitate cooling of the tissue of the first ablation zone 106.

Following ablation of the first ablation zone 106, the laser fiber displacement system 100 may be remotely transitioned or repositioned to the second ablation zone state where the distal portion of the laser fiber 190 is disposed adjacent the targeted second ablation zone 107, as shown in FIG. 5. In other words, the laser fiber 190 may be displaced (such as pulled back or displaced proximally) without a practitioner entering the MRI room and manually pulling back the laser fiber 190. In the transition to the illustrated second ablation zone state, the carriage 114 is displaced proximally (direction of arrow) by the motor 119 (not shown). The motion of the motor 119 may be controlled by a computer disposed outside of the MRI room. A control signal may be sent through the communication cable 195, to the communication member 126 (not shown), to the motor controller 124 (not shown) and to the motor 119. The control signal can activate the motor 119 and control the position of the laser fiber 190 such that the distal portion of the laser fiber 190 is at a desired location relative to the lesion 105. The motor 119 displaces the carriage 114 and clamp 115 proximally resulting in the laser fiber 190 being pulled back or displaced proximally through the cooling catheter 180, the manifold 161 of the tubing set 160, the sealing member 150, and the sleeve 140.

In the second ablation zone state, the distal portion of the laser fiber 190 is positioned adjacent the second ablation zone 107. The cooling catheter 180 may be in the same position relative to the lesion 105 as the first ablation zone state. Said differently, in some procedures, the cooling catheter 180 remains longitudinally stationary while the laser fiber 190 is pulled back despite a proximally directed force being applied by the laser fiber drawback system including a force applied to the sleeve 140. The proximally directed force may be generated by at least a drag force as the laser fiber 190 is pulled through the sealing member 150. As discussed above, the sleeve 140 is configured to resist longitudinal compression. Therefore, when a proximally directed force is applied to the sleeve 140, the sleeve 140 substantially maintains its length resulting in the cooling catheter 190 remaining substantially longitudinally stationary. In other words, the system may be configured such that a proximally directed force applied to the laser fiber 190 may result in proximally directed forces acting on one or more components of the laser displacement system. For example, when a proximally directed force is applied to the laser fiber 190 the laser fiber 190 may interact with the sealing member 150 or interior surfaces of the sleeve 140. The proximally directed forces may apply a compression force to the sleeve 140. However, the sleeve 140 may have sufficient rigidity to resist compression and maintain the relative position of the laser displacement system components (other than the laser fiber 190) as the laser fiber 190 is displaced.

When the distal portion of the laser fiber 190 is repositioned to be adjacent the second ablation zone 107, MRI may be used to confirm the position of the laser fiber 190. Laser energy is transmitted through the laser fiber 190. The laser energy may be diffused through the tissue of the second ablation zone 107 such that the tissue absorbs the energy and is heated, resulting in ablation or destruction of the tissue. Fluid may be delivered to and withdrawn from the second ablation zone 107 through the tubing set 160 to facilitate cooling of the tissue of the second ablation zone 107. These steps, or a subset of these steps, may be repeated to treat other portions of the tissue, for example until the entire lesion 105 has been ablated.

Alternatively, in some embodiments the laser energy is transmitted continuously through the laser fiber 190 while the laser fiber 190 is retracted through the lesion 105 with continuous motion. Such embodiments form an ablation zone through the lesion 105 that is substantially cylindrical in shape. The rate of retraction may be controlled based on the ablation rate to facilitate ablation of the tissue of the lesion 105 without ablating tissue surrounding the lesion or to prevent insufficient tissue ablation. For example, the rate of retraction may be increased where portions of the desired ablation zone are smaller than other portions of the desired ablation zone. Alternatively, the rate of retraction may be reduced when the desired ablation zone has a diameter that is larger than other portions. Similarly, for denser tissues, the rate of retraction may be slowed, whereas for less dense tissues the rate of retraction may be increased.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A laser fiber displacement system, comprising:
a displacement device, comprising:
a housing;
a linear slide coupled to the housing;
a carriage slidingly coupled to the linear slide, wherein the carriage is configured to longitudinally move relative to the housing along the linear slide between a proximal position of the carriage and a distal position of the carriage; and
a clamp coupled to the carriage, the clamp comprising a slot extending into a side of the clamp, wherein the slot extends along a longitudinal length of the carriage, wherein the slot is configured to selectively receive a laser fiber, and wherein the clamp is configured to apply a clamping force that secures the laser fiber to the carriage; and
a sleeve comprising a lumen configured to receive the laser fiber within the lumen of the sleeve, the sleeve configured to selectively couple a cooling catheter to the displacement device,
wherein the displacement device is configured to longitudinally displace the laser fiber relative to the cooling catheter through the lumen as the carriage longitudinally moves between the proximal position of the carriage and the distal position of the carriage, and wherein the sleeve is configured to resist longitudinal compression such that the cooling catheter remains stationary relative to the housing as the carriage longitudinally moves between the proximal position of the carriage and the distal position of the carriage.

2. The system of claim 1, wherein the displacement device comprises:
a motor coupled to the carriage, wherein the motor is configured to longitudinally move the carriage between the proximal position of the carriage and the distal position of the carriage; and
a power source electrically interconnected to the motor, wherein the power source is configured to provide electrical power to the motor.

3. The system of claim 2, wherein the displacement device further comprises a motor controller and a communication member, wherein the communication member is an optical to serial converter.

4. The system of claim 2, wherein the motor is any one of a piezo linear motor, a piezo rotation motor, a piezo motor, or a stepper motor.

5. The system of claim 2, wherein the power source comprises any one of a disposable battery or a rechargeable battery.

6. The system of claim 5, wherein the power source comprises a lithium polymer battery.

7. The system of claim 1, wherein the sleeve comprises:
a hollow elongate body comprising the lumen;
a first connector disposed at a proximal end of the hollow elongate body, wherein the sleeve is coupled to the displacement device at the first connector; and
a second connector disposed at a distal end of the hollow elongate body, wherein the cooling catheter is arranged distally of the second connector; and
wherein the hollow elongate body is configured to resist longitudinal compression.

8. The system of claim 7, wherein the hollow elongate body comprises any one of nylon, polyethylene, or polypropylene.

9. The system of claim 1, further comprising a communication cable, wherein the communication cable comprises an optical fiber.

10. The system of claim 1, wherein the laser fiber displacement system is configured to be used in a magnetic resonance environment.

11. The system of claim 1, further comprising:
a sealing member selectively coupled to the sleeve; and
a tubing set selectively coupled to the sealing member.

12. The system of claim 11, wherein the sealing member is configured to selectively fluidly seal around the laser fiber and to allow displacement of the laser fiber relative to the seal member.

13. The system of claim 11, wherein the tubing set comprises:
a manifold comprising an inflow port and an outflow port;
an extension tube coupled to each of the inflow port and the outflow port;
an elongate inflow tubing coupled to the extension tube of the inflow port; and
an elongate outflow tubing coupled to the extension tube of the outflow port.

14. The system of claim 1, wherein the laser fiber is prevented from rotating as the carriage longitudinally moves between the proximal position of the carriage and the distal position of the carriage.

15. A method of ablating a tissue, comprising:
inserting a laser fiber and a cooling catheter into a target ablation region;

transmitting laser energy through the laser fiber to ablate a first tissue zone in the target ablation region;

displacing, via a displacement device of a laser fiber displacement system, the laser fiber from the first tissue zone to a second tissue zone in the target ablation region, wherein the displacement device comprises:

a housing;

a linear slide coupled to the housing;

a carriage slidingly coupled to the linear slide, wherein the carriage is configured to longitudinally move relative to the housing along the linear slide between a proximal position of the carriage and a distal position of the carriage; and a clamp coupled to the carriage, the clamp comprising a slot extending into a side of the clamp, wherein the slot extends along a longitudinal length of the carriage, wherein the slot is configured to selectively receive the laser fiber, wherein the clamp is configured to apply a clamping force that secures the laser fiber to the carriage, wherein displacing the laser fiber comprises longitudinally displacing the laser fiber through a sleeve of the laser fiber displacement system that is coupled to the cooling catheter as the carriage longitudinally moves between the proximal position of the carriage and the distal position of the carriage, and wherein the sleeve resists longitudinal displacement of the cooling catheter; and transmitting laser energy through the laser fiber to ablate a second tissue zone in the target ablation region.

16. The method of claim 15, wherein displacing the laser fiber comprises remotely activating the displacement device.

17. The method of claim 15, further comprising disposing the laser fiber displacement system within a magnetic resonance environment.

18. The method of claim 15, further comprising:

inserting the cooling catheter into a patient, wherein a distal portion of the cooling catheter is adjacent the first tissue zone; and disposing the laser fiber through the cooling catheter, wherein a distal portion of the laser fiber extends distally beyond the distal portion of the cooling catheter.

19. A laser fiber displacement device, comprising:

a housing;

a linear displacement member comprising:

a linear slide coupled to the housing;

a carriage slidingly coupled to the linear slide, wherein the carriage is configured to longitudinally move relative to the housing along the linear slide between a proximal position of the carriage and a distal position of the carriage;

a clamp coupled to the carriage, the clamp comprising a slot extending into a side of the clamp, wherein the slot extends along a longitudinal length of the carriage, wherein the slot is configured to selectively receive a laser fiber, the laser fiber being configured for sliding movement within a cooling catheter; and a motor coupled to the carriage, wherein the motor is configured to longitudinally move the carriage between the proximal position of the carriage and the distal position of the carriage; and a sleeve configured to couple to the housing and comprising a lumen, the sleeve configured to selectively couple to the cooling catheter and receive the laser fiber through the lumen, wherein the sleeve is configured to resist longitudinal compression and maintain a position of the cooling catheter relative to the housing when the linear displacement member displaces the laser fiber relative to the cooling catheter through the lumen as the carriage longitudinally moves between the proximal position of the carriage and the distal position of the carriage.

20. The laser fiber displacement device of claim 19, wherein the laser fiber displacement device is configured to be used in a magnetic resonance environment, and wherein the laser fiber is prevented from rotating as the carriage longitudinally moves between the proximal position of the carriage and the distal position of the carriage.

* * * * *